US005767257A

United States Patent [19]
Schafermeyer et al.

[11] Patent Number: 5,767,257
[45] Date of Patent: Jun. 16, 1998

[54] METHODS FOR PRODUCING POLYOL FATTY ACID POLYESTERS USING ATMOSPHERIC OR SUPERATMOSPHERIC PRESSURE

[75] Inventors: Richard Gerard Schafermeyer; Patrick Joseph Corrigan, both of Hamilton County; Corey James Kenneally, Warren County; James Earl Trout, Butler County, all of Ohio

[73] Assignee: The Procter & Gamble Company, Cincinnati, Ohio

[21] Appl. No.: 684,119

[22] Filed: Jul. 19, 1996

[51] Int. Cl.⁶ .............................. C07H 13/02; C07H 1/00
[52] U.S. Cl. .................. 536/18.6; 536/18.5; 536/119; 536/123.13; 536/124
[58] Field of Search .................. 536/18.5, 18.6, 536/119, 123.13, 124; 554/227, 228, 229

[56] References Cited

U.S. PATENT DOCUMENTS

| | | | |
|---|---|---|---|
| 3,347,848 | 10/1967 | Ismail et al. | 536/119 |
| 3,353,966 | 11/1967 | Hugenberg et al. | 536/119 |
| 3,714,144 | 1/1973 | Feuge et al. | 536/119 |
| 3,963,699 | 6/1976 | Rizzi et al. | 536/119 |
| 3,996,206 | 12/1976 | Parker et al. | 536/119 R |
| 4,032,702 | 6/1977 | James | 536/119 |
| 4,298,730 | 11/1981 | Galleymore et al. | 536/119 |
| 4,334,061 | 6/1982 | Bossier, III. | 536/119 |
| 4,348,540 | 9/1982 | Ferris et al. | 536/119 |
| 4,517,360 | 5/1985 | Volpenhein | 536/119 |
| 4,518,772 | 5/1985 | Volpenhein | 536/119 |
| 4,773,881 | 9/1988 | Nieuwenhuis et al. | 536/119 |
| 4,806,632 | 2/1989 | McCoy et al. | 536/124 |
| 5,043,438 | 8/1991 | Buter | 536/119 |
| 5,158,796 | 10/1992 | Bernhardt et al. | 426/549 |
| 5,231,199 | 7/1993 | Willemse | 554/174 |

FOREIGN PATENT DOCUMENTS

| | | |
|---|---|---|
| 0062565 | 10/1982 | European Pat. Off. . |
| 0315265 | 5/1989 | European Pat. Off. . |
| 0383404 | 8/1990 | European Pat. Off. . |
| 50-135016 | 10/1975 | Japan . |
| 1499989 | 2/1978 | United Kingdom . |
| 9204361 | 3/1992 | WIPO . |
| WO9311141 | 6/1993 | WIPO . |

OTHER PUBLICATIONS

Journal of the American Chemists' Society, "A Solvent–Free Synthesis of Sucrose Polyesters," George P. Rizzi and Harry M. Taylor, Apr. 1978, see pp. 398–401.

Prentice–Hall International Series in the Physical and Chemical Engineering Sciences, "Basic Principles and Calculations in Chemical Engineering, Second Edition" David M. Himmelblau, 1967, 1967, see pp. 96–97.

O. Levenspiel, "Chemical Reaction Engineering," John Wiley & Sons, New York (1972), see pp. 124–139.

Journal of the American Chemists' Society, vol. 47, "Preparation of Sucrose Esters by Interesterification," R.O. Feuge et al., see pp. 56–60.

*Primary Examiner*—John Kight
*Assistant Examiner*—Howard C. Lee
*Attorney, Agent, or Firm*—Gerry S. Gressel; Karen F. Clark

[57] ABSTRACT

Methods for the solventless transesterification of a polyol comprise reacting polyol with fatty acid alkyl ester in the presence of a basic catalyst to produce polyol fatty acid polyester product and lower alkyl alcohol by-product, wherein a majority of the polyol is fully esterified. The reaction is conducted in a reactor at a temperature in the range of from about 60° to about 180° C. and at atmospheric or superatmospheric pressure. An inert gas is sparged through the reactor with sufficient mass transfer surface area contact between the inert gas and reactor liquid to transfer the lower alkyl alcohol by-product from a liquid mixture of reactant and product to the inert gas and promote full esterification of a majority of the polyol without the use of vacuum pressure.

26 Claims, No Drawings

METHODS FOR PRODUCING POLYOL FATTY ACID POLYESTERS USING ATMOSPHERIC OR SUPERATMOSPHERIC PRESSURE

FIELD OF THE INVENTION

The present invention is directed to methods for transesterification of a polyol to produce polyol fatty acid polyesters, wherein the methods are conducted under atmospheric or superatmospheric pressure. More particularly, the present invention is directed to such methods wherein a majority of the polyol is fully esterified without the use of vacuum pressure.

BACKGROUND OF THE INVENTION

Processes for the synthesis of polyol fatty acid polyesters by the transesterification of a polyol are well known in the art. For example, the Rizzi et al. U.S. Pat. No. 3,963,699 discloses a solvent-free transesterification process comprising two main steps, each of which is conducted in a batch reactor. In the first step, a mixture of polyol, a fatty acid lower alkyl ester, an alkali metal fatty acid soap, and a basic catalyst are heated to form a homogenous melt of partially esterified polyol and unreacted starting materials. Rizzi et al. broadly disclose the use of a pressure of from about 0.1 mm Hg to about 760 mm Hg, and preferably from about 0.5 mm Hg to about 25 mm Hg, in their first step. In a second step, excess fatty acid lower alkyl esters are added to the reaction product of the first step to form the polyol fatty acid polyester. Rizzi et al. similarly disclose that their second step is conducted at a pressure of from about 0.1 m Hg to about 760 mm Hg, with the range from about 0.5 mm Hg to about 25 mm Hg being preferred. Rizzi et al. further disclose that a lower alcohol is formed as by-product of the reaction and, in order to promote the reaction, the alcohol by-product is preferably removed. Many removal techniques are acknowledged by Rizzi et al. as being known in the art; Rizzi et al. indicate that vacuum removal, both with and without an inert gas sparging, has been found to promote the reaction, and that simple distillation under atmospheric pressure may also be sufficient.

The Volpenhein U.S. Pat. Nos. 4,517,360 and 4,518,772 disclose further solvent-free transesterification processes for producing higher polyol fatty acid polyesters. In U.S. Patent No. 4,517,360, Volpenhein discloses the use of potassium carbonate, sodium carbonate or barium carbonate as a catalyst and the use of methyl, 2-methoxy ethyl or benzyl fatty acid ester. In U.S. Pat. No. 4,518,772, Volpenhein discloses the use of preferred molar ratios of soap to polyol of from about 0.6:1 to about 1:1 in the first step of the two step process. Volpenhein also employs a two step batch reaction process, with the first step being conducted at a pressure of from about 0.1 mm Hg to about 760 mm Hg, preferably from about 0.5 mm Hg to about 25 mm Hg, and the second step being conducted at a pressure of from about 0.1 mm Hg to about 10 mm Hg. Volpenhein also discloses the advantage of removing lower alcohol by-product to promote the transesterification reaction.

The Buter U.S. Pat. No. 5,043,438 discloses a process for the synthesis of polyol fatty acid esters by reacting a polyol and a fatty acid lower alkyl ester under substantially solvent-free and reduced pressure conditions. Buter discloses that the process employs a pre-reactor in which the reaction mixture is in steady state with mass-balanced in-going reactant streams and out-going product streams having a polyol conversion of 1% or more. Buter further discloses that the process reduces initial viscosity and/or de-mixing problems caused by the heterogeneous nature of the reactant mixture and the use of soap emulsifiers.

In practice, the polyol transesterification reaction is commonly conducted under vacuum in order promote removal of the lower alkyl alcohol by-product, i.e., methanol. In order to maintain the low pressure in the reaction system, large and expensive vacuum equipment systems have been required. Particularly, in large scale production, even lower vacuum pressures are required so that the necessary equipment and operating costs are a significant factor. Additionally, because the vacuum systems have been susceptible to air leaks, the polyol fatty acid polyester product is susceptible to degradation by incoming air during manufacturing processes employing vacuum systems. Specifically, air can undesirably darken the polyol fatty acid polyester product and/or affect oxidation which adversely influences product flavor.

Polyol fatty acid polyesters are increasingly being employed in various applications, including as low-calorie fats in many food products. Accordingly, the demand for polyol fatty acid polyesters suitable for human consumption is rapidly increasing. As a result, processes for more efficient and economical synthesis of such polyol fatty acid polyesters are necessary and desirable.

SUMMARY OF THE INVENTION

Accordingly, it is an object of the present invention to provide improved methods for the production of polyol fatty acid polyesters, particularly by the transesterification of polyol reactant. It is a further object of the invention to provide processes for the production of polyol fatty acid polyesters, which processes overcome disadvantages of conventional processes wherein the transesterification reaction is conducted under vacuum conditions. It is a related object of the present invention to provide improved methods for the production of polyol fatty acid polyesters, which processes have improved efficiency and/or are more economical as compared with various conventional processes for the production of polyol fatty acid polyesters.

These and additional objects are provided by the methods of the present invention which are directed to the solventless transesterification of a polyol. More specifically, the methods according to the present invention comprise reacting polyol with fatty acid alkyl ester in the presence of a basic catalyst to produce polyol fatty acid polyester product and lower alkyl alcohol by-product, wherein a majority of the polyol is fully esterified, i.e., all of the hydroxyl groups are esterified in greater than 50 weight percent of the polyol. In accordance with important features of the invention, the reaction is conducted in a reactor at a temperature in the range of from about 60° to about 180° C. and at atmospheric or superatmospheric pressure, and an inert gas is sparged through the reactor with sufficient mass transfer surface area contact between the inert gas and a liquid mixture of reactant and product to transfer the lower alkyl alcohol by-product from the liquid mixture to the inert gas and promote full esterification of a majority of the polyol, without the use of vacuum pressure.

In a more specific embodiment of the present methods, the polyol which is employed in the transesterification reactions comprises sucrose, and the reaction is conducted at atmospheric or superatmospheric pressure. The inert gas is sparged through the reactor with sufficient agitation to transfer lower alkyl alcohol by-product from a liquid mixture of reactant and product to the inert gas and promote conversion of a majority of the sucrose to octaester without the use of vacuum pressure.

The present methods are advantageous in at least several respects. Because the methods are conducted at atmospheric or superatmospheric pressures, expensive vacuum systems which have been employed in various conventional methods are avoided, thereby resulting in lower equipment costs and lower operating costs. Additionally, because the present methods are not conducted under vacuum, the equipment employed in the present methods is not as susceptible to leakage of air into the processing environment, whereby good quality of polyol fatty acid polyester product is maintained and product degradation owing to air leakage into the manufacturing system is avoided. The methods according to the present invention may also result in high conversion to the desired product in relatively short reaction times, particularly as compared with conventional processes, thereby allowing the use of smaller reaction equipment or providing increased yields for a specified production period. Additionally, shorter reaction times generally lead to better color in the polyol fatty acid polyester product, whereby the methods of the present invention may be employed to provide improved product. Additionally, the methods according to the present invention allow easy removal of the lower alkyl alcohol by-product, i.e., methanol, from the inert sparging gas, thereby facilitating recycling of the inert gas stream and allowing a more simple design of the inert gas handling equipment, particularly as compared with the inert gas handling requirements of various conventional processes.

These and additional objects and advantages will be more fully discussed in the following detailed description.

DETAILED DESCRIPTION

The present invention is directed to improved methods for the solventless transesterification of a polyol. According to the present methods, polyol is reacted with fatty acid lower alkyl ester in the presence of a basic catalyst to produce polyol fatty acid polyester product and lower alkyl alcohol by-product. In accordance with an important feature of the present methods, a majority of the polyol is fully esterified.

Basic design criteria for methods for the transesterification reaction are disclosed in the Rizzi et al. U.S. Pat. No. 3,963,699 and the Volpenhein U.S. Pat. Nos. 4,517,360 and 4,518,772, and the design criteria teachings of these references are incorporated herein by reference.

As used herein, the term "polyol" is intended to include any aliphatic or aromatic compound containing at least two free hydroxyl groups. In practicing the processes disclosed herein, the selection of a suitable polyol is simply a matter of choice. For example, suitable polyols may be selected from the following classes: saturated and unsaturated straight and branched chain linear aliphatic; saturated and unsaturated cyclic aliphatic, including heterocyclic aliphatic; or mononuclear or polynuclear aromatics, including heterocyclic aromatics. Carbohydrates and nontoxic glycols are preferred polyols. Monosaccharides suitable for use herein include, for example, mannose, galactose, arabinose, xylose, ribose, apiose, rhamnose, psicose, fructose, sorbose, tagitose, ribulose, xylulose, and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharide suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also preferred for use herein. The sugar alcohols most widely distributed in nature and suitable for use herein are sorbitol, mannitol and galactitol.

Particularly preferred classes of materials suitable for use herein include the monosaccharides, the disaccharides and sugar alcohols. Preferred carbohydrates and sugar alcohols include xylitol, sorbitol and sucrose.

Sugar alkyl ethers, polyalkoxylated glycerol and polyglycerol esters can also be used.

In one embodiment, it is preferable to employ polyol which has at least three hydroxyl groups, and more preferably the polyol which is employed in the methods of the present invention has at least 4 hydroxyl groups. A particularly preferred polyol for use in the present methods is sucrose.

The fatty acid lower alkyl esters which are employed as reactants in the present processes include the methyl and ethyl esters of fatty acids containing about eight or more carbon atoms, preferably from 8 to about 24 carbon atoms, and mixtures of such esters. Suitable esters can be prepared by the reaction of diazoalkanes and fatty acids, or derived by alcoholysis from the fatty acids naturally occurring in fats and oils. Fatty acid esters suitable for use herein may be derived from either saturated or unsaturated fatty acids. Suitable preferred saturated fatty acids include, for example, capric, lauric, palmitic, stearic, behenic, elaidic, isomyristic, isomargaric, myristic, caprylic, and anteisoarachadic. Suitable preferred unsaturated fatty acids include, for example, maleic, linoleic, licanic, oleic, linolenic, and erythrogenic acids. Mixtures of fatty acids derived from unhydrogenated or partially hydrogenated soybean oil, sunflower oil, rapeseed oil, high erucic acid, palm oil, coconut oil, peanut oil, canola oil, tallow oil, corn oil, cottonseed oil and fatty hydrogenated rapeseed oil are especially preferred for use herein. Methyl esters are the preferred fatty acid esters for use herein, since their use in the processes herein tends to result in high yields of polyol fatty acid polyesters.

In one embodiment, the entire amount of fatty acid lower alkyl ester may be combined with polyol reactant. In an alternate embodiment, however, a portion of the fatty acid lower alkyl ester is added to the reaction system after polyol has been reacted with an initial feed of fatty acid lower alkyl ester. This embodiment is well known in the art and commonly additional fatty acid lower alkyl ester is added to the reaction system at a point wherein approximately 25% to 50% of the polyol hydroxyl groups have been esterified.

The catalyst which is employed in the processes of the present invention may be any one of a number of basic catalysts known in the art for use in the transesterification of polyol. Preferably, the catalyst is selected from the group consisting of alkali metals and alkali metal compounds, including sodium, lithium or potassium, alloys of two or more of these metals, or carbonates, bicarbonates, alkoxides, or hydroxides of these metals or mixtures thereof. In a further preferred embodiment of the present processes, the basic catalyst is a carbonate, bicarbonate, alkoxide or hydride of sodium or potassium, or comprises mixtures of two or more of these compounds.

Owing to the relative phase incompatibility between the polyol and the fatty acid lower alkyl ester reactants, it is often advantageous to employ an emulsifier which assists in bringing the polyol and the fatty acid lower alkyl ester into increased contact for facilitating the transesterification reaction of the polyol. As is known in the art, a particularly preferred emulsifier comprises alkali metal fatty acid soap. As used herein, the term "alkali metal fatty acid soap" is intended to include the alkali metal salts of saturated and unsaturated fatty acids having from about 8 to about 22 carbon atoms. Accordingly, suitable alkali metal fatty acid soaps include, for example, the lithium, sodium, potassium, rubidium and cesium salts of fatty acids such as capric, lauric, myristic, palmitic, licanic, parinaric, behenic and stearic acids. Mixtures of fatty acids derived from soybean oil, sunflower oil, safflower oil and corn oil are preferred for use herein. Particularly preferred alkali metal fatty acid soaps include, for example, the potassium soap made from soybean oil fatty acids and the sodium soap made from sunflower oil fatty acids.

Also effective as emulsifiers are polyol mono-, di, and triesters. Since these are produced during the first part of the reaction, a preferred method of running the reaction is to add sucrose, fatty acid lower alkyl esters, and alkali catalyst to a reaction vessel where polyol mono-, di-, and/or triesters are present. Other emulsifiers such as soaps are not required. This can be achieved in a batch process, a semibatch process, or more preferably in a continuous process, where the feed materials are continuously added to a continuous backmixed reactor containing polyol mono-, di-, or triesters.

The feed rates of the polyol and fatty acid lower alkyl ester reactants, and the ratios of reactants to catalysts and emulsifier, if employed, may be varied in accordance with desired reactants and reaction products. Suitable ratios are well known in the art as taught, for example, by Rizzi et al. and Volpenhein, previously incorporated herein by reference.

It is well known in the art that the transesterification reaction of the polyol with a fatty acid lower alkyl ester results in the formation not only of the polyol fatty acid polyester, but also in the formation of a lower alkyl alcohol by-product. When fatty acid methyl esters are employed as reactants, the lower alkyl alcohol by-product comprises methanol. It is also well known in the art that removal of the lower alkyl alcohol by-product such as methanol promotes further transesterification reaction. As will be described in further detail below, an important feature of the present invention is that improved removal of the lower alkyl alcohol during the transesterification reaction is achieved, specifically without the use of a vacuum as has been conventionally employed in prior art practices.

More particularly, in accordance with important features of the present methods, the transesterification reaction is conducted in a reactor at a temperature in the range of from about 60° to about 180° C. and at atmospheric or superatmospheric pressure. A preferred temperature range is from about 90° to about 150° C., and more preferably from about 120° to about 150° C., particularly when the polyol is sucrose. A preferred average reactor pressure is from about 760 mm Hg to about 2500 mm Hg, more preferably from about 760 mm Hg to about 1500 mm Hg. The pressure will vary with the reactor dimensions, particularly the height. Importantly, the pressure must be high enough to overcome the pressure change of the reactor (liquid head plus $\Delta p$). An inert gas is sparged through the reactor with sufficient mass transfer surface area contact between the gas and liquid therein to transfer the lower alkyl alcohol by-product from a liquid mixture of reactant and product to the inert gas and promote full esterification of a majority of the polyol without the use of vacuum pressure. Any inert gas having a suitable partial pressure sufficient to affect transfer of the lower alkyl alcohol from the liquid phase to the gas phase may be employed. Particularly preferred inert gases for use in the processes of the present invention include nitrogen, carbon dioxide and aliphatic hydrocarbons, for example, hexane.

The present inventors have discovered that an increase in the mass transfer surface area between the liquid which contains a mixture of reactants, products and the lower alkyl alcohol by-product and a sparging gas achieves sufficient removal of the lower alkyl alcohol by-product from the liquid mixture, thereby promoting the transesterification reaction, without the use of a vacuum system as is commonly employed in prior art processes. Various techniques for increasing the mass transfer surface area between the liquid mixture in which the lower alkyl alcohol by-product is contained and the inert sparging gas will be apparent to those of ordinary skill in the art in view of the present detailed description. For example, the increase in mass transfer surface area can be self-induced agitation, i.e., use of a bubble column, a packed column, or the like increases the interfacial area between gas and liquid. Alternatively, or in addition, various agitator or mixing equipment may be employed.

It is preferred, although not required, that the entire transesterification reaction is conducted under the atmospheric or superatmospheric conditions, with inert gas sparging, as discussed above. In embodiments wherein the atmospheric or super atmospheric pressure and inert gas sparging are not maintained throughout the entire transesterification reaction, these conditions are employed at least during a portion of the later portion of the transesterification reaction, i.e. for the reaction subsequent to about a 50% degree of conversion, and more preferably, subsequent to about a 30% degree of conversion. The degree of conversion refers to the percentage of polyol hydroxyl groups which have been esterified. In one embodiment, atmospheric or superatmospheric pressure with inert gas sparging is employed in the production of sucrose polyester until at least a majority of polyol is fully esterified, after which vacuum pressure, with or without inert gas sparging is employed to obtain the desired octaester conversion of at least about 70 percent.

In one embodiment the transesterification reaction may be conducted in a packed column, whereby the packing increases the gas-liquid surface contact area between the inert sparging gas and the liquid mixture of polyol and fatty acid lower alkyl ester reactants, partially esterified polyol, fully esterified polyol product and lower alkyl alcohol by-product. In such an embodiment, it is preferable that the inert sparging gas run counter current to the liquid mixture of reactants and products. Packed columns of this type are well known in the art and are discussed, for example, by Perry et al., *Chemical Engineer's Handbook*, Fifth Edition, MacGraw-Hill, 1973, pp.18–19 through 18–49, which are incorporated herein by reference. In this embodiment, all or only a portion of the transesterification reaction may be conducted in such a packed column reactor. It is preferred that at least the later portion of the transesterification reaction, i.e. subsequent to about a 50% degree of conversion, is conducted in the packed column.

Another reactor suitable for conducting the transesterification reaction is a falling film reactor. In a falling film reactor, the liquid mixture of reactants, partially esterified polyol, fully esterified polyol and lower alkyl alcohol by-product is fed to the top of tubes and flows down the tube walls as a film. The inert sparging gas is directed upwardly through the tubes, thereby providing increased contact surface area between the liquid mixture and the inert sparging gas to maximize mass transfer of the lower alkyl alcohol from the liquid mixture to the sparging gas and promote further esterification reaction. Such reactors are also well known in the art and disclosed by Perry et al., supra, pp. 11–28 through 11–30.

In an alternate embodiment, the transesterification reaction may be conducted in one or more tank reactors provided with gas dispersers and agitators. Both the gas dispersers and the agitators increase contact surface area between the liquid reaction mixture and the sparging gas in order to increase mass transfer of a lower alkyl alcohol from the liquid reaction mixture to the sparging gas. Additionally, both gas dispersers and liquid agitators suitable for use in the present methods are known in the art.

A multistage column reactor, particularly such a reactor having counter current liquid and gas transfer means between stages, is also suitable for conducting the transesterification reaction according to the present invention. Although various multistage columns suitable for use in the present methods are known in the art, a particularly preferred multistage column is disclosed in the Kenneally et al. copending U.S. application Ser. No. 08/683,899, incorporated herein by reference.

In accordance with the present methods, selection of the particular type of reactor is not critical as long as the reactor provides for increased surface area contact between the liquid reaction mixture and the sparging gas, thereby allowing increased mass transfer of the lower alkyl alcohol from the liquid reaction mixture to the sparging gas and promoting the further transesterification reaction. Accordingly, it is also within the scope of the present invention that the transesterification reaction is conducted in more than one reactor, including a combination of different types of reactors in order to maximize the mass transfer contact surface area between the liquid reaction mixture and the sparging gas, particularly during the later portion of the transesterification reaction.

Owing to the use of the inert sparging gas and the provision of sufficient agitation in the transesterification reactor, the transesterification reaction may be conducted at atmospheric or superatmospheric pressure in order to obtain a product wherein a majority of the polyol is fully esterified, without the use of vacuum pressure. A majority of the polyol being fully esterified means that at least 50% of the polyol reactant is fully esterified, i.e., all of the hydroxyl groups of the polyol are esterified. In a preferred embodiment, wherein the polyol is sucrose and the desired product is octaester, it is preferred that at least 70 weight percent of the esters produced in the reaction are octaester. Additionally, it is further preferred that the degree of conversion of the sucrose hydroxyl group to ester groups is at least 95%, i.e., at least 95% of all of the initial sucrose hydroxyl groups are esterified.

As noted above, in a preferred embodiment, the transesterification reaction is conducted at an average reactor pressure of from about 760 mm Hg, i.e. ambient atmospheric pressure, to about 2500 mm Hg. Preferably the average reactor pressure is from about 760 to 1500 mm Hg. Although pressures greater than about 2500 mm Hg can be employed, generally, such higher pressures are not preferred owing to the higher costs of the necessary equipment and the higher operation costs associated with such a system. Pressures within the range of from about 760 mm Hg to about 2500 mm Hg are also advantageous in that oxygen-containing ambient air is prevented from entering the reaction system, whereby degradation of the polyester product by ambient air is minimized in the reaction system. Because oxygen entering into the reaction system can degrade the polyester product's color and/or taste, the ability to exclude ambient air from the reaction system in an easy manner by use of atmospheric or superatmospheric pressures in the reaction system is an additional important advantage of the present methods.

Thus, the methods of the present reaction are advantageous in that vacuum systems which have been employed in conventional prior art systems are avoided. Additionally, expensive methanol recovery from dilute aqueous streams, which is required when using stream injectors for vacuum, is avoided according to the invention. The great expense of both the vacuum system equipment and the operation of the vacuum systems are thereby avoided by the present methods. Additionally, owing to the increase in mass transfer of the lower alkyl alcohol by-product from the liquid reaction mixture to the sparging gas in accordance with the present methods, the transesterification reaction can proceed to high conversion in shorter reaction time as compared with prior art processes, thereby allowing design of smaller reaction equipment or provision of increased product quantities for a specific production period. Additionally, the present methods can provide a higher quality product since shorter reaction times generally lead to better product color and/or product flavor.

Because the present methods are conducted at atmospheric or superatmospheric pressure, removal of the lower alkyl alcohol, for example methanol, from the inert sparging gas, subsequent to the exiting of the gas from the transesterification reactor, is simplified. The lower alkyl alcohol may be removed from the inert sparging gas using one or more of the techniques commonly known in the art. For example, in one embodiment, the inert sparging gas containing the lower alkyl alcohol therein may be subjected to cooling, after which the cooled gas is passed through an absorbent material, for example carbon black, to remove the lower alkyl alcohol from the sparging gas. In a preferred embodiment, substantially all of the lower alkyl alcohol by-product is removed from the inert sparging gas, whereby at least a portion of the inert gas may be recycled to the transesterification reactor for further use therein. Preferably, the inert gas which is recycled has a lower alkyl alcohol partial pressure of less than about 10 mm Hg, more preferably less than about 5 mm Hg and further preferably less than about 2 mm Hg.

As noted above, in order to affect and promote the transesterification reaction, heat is supplied to the reactor so that the reaction can be conducted at an elevated temperature in the range of from about 60° to about 180° C., more preferably from about 120° to about 150° C. In one embodiment, this elevated temperature can be provided by heating the contents of the reactor in situ. Alternatively, or in addition, one or more of the feed streams to the reactor may be preheated whereby polyol, fatty acid lower alkyl ester and/or the inert gas is preheated to a temperature in the range of from about 60° to about 180° C. In one embodiment, a heat exchanger may be employed wherein warm inert gas which is removed from the reactor may be provided in heat exchange contact with ingoing gas or reactants, whereby the warm inert gas is cooled and the ingoing gas or reactants are at least partially heated thereby.

The processes of the present invention advantageously employ inert gas in an amount which is significantly reduced as compared with prior art processes employing inert gas sparging. For example, suitable weight ratios of inert gas to liquid reactant feed in the processes according to the present invention may be in the range of less than about 4:1, preferably less than about 3:1, and more preferably less than about 2.5:1.

In accordance with conventional processes, the polyol fatty acid polyester product of the present processes may be subjected to washing, drying, bleaching, filtration, separation and/or deodorization processing steps and/or blended with other components for providing a final product.

The following examples are set forth to illustrate various features of the present processes. In the examples and otherwise throughout the present specification, parts and percentages are by weight unless otherwise specified.

EXAMPLE 1

This example describes the use of a reaction column to perform both stages of the transesterification reaction, i.e., the initial esterification of sucrose to sucrose lower esters, and the further reaction to a high degree of esterification. A column is constructed that contains two sections, one on top of the other. The top section is designed for the initial esterification. This section consists of a 9-inch diameter, 24-inch long glass column divided into 2 sections by two plates, each of which is about 9-inches in diameter and has a center hole about 1-inch in diameter. Each segment is about 12 inches high and has a 6-bladed turbine agitator that is approximately one half the diameter of the column. Fewer segments in this section of the column lead to more backmixing, which is desirable in the initial sucrose esterification. The lower section of the column is about 6-inches in diameter and divided into 14 sections. The lower section is designed for a second stage of the reaction, i.e., the esterification of sucrose lower esters to sucrose polyesters. A single agitator shaft runs through both sections of the column, and turns all of the agitators simultaneously. Both sections have heating mantles.

Reaction material for the first stage of the reaction is fed into the top of the column and travels downward through the column through the center hole of each of the successive section plates. The feed material comprises sucrose, potassium carbonate, and cottonseed fatty acid methyl esters in the following molar ratios: fatty acid methyl ester:sucrose of 5:1, potassium carbonate:sucrose of 0.1:1. Sucrose is emulsified into the methyl esters by sucrose mono-, di-, and triesters that are present in the top section of the column. The reaction material flows downward by gravity from the top section of the column to the narrower lower section of the column. At the top of the narrower lower section of the column, additional cottonseed fatty acid methyl esters are added to raise the molar ratio of total methyl esters to initial sucrose to about 11:1. Additional potassium carbonate is added to raise the molar ratio of total potassium carbonate to initial sucrose to about 0.2:1. The resulting liquid mixture flows down the lower section of the column for further reaction. Nitrogen is introduced at the bottom of the column and travels upward through the column, through the center holes, counter current to the liquid flow. In each segment, the nitrogen is dispersed into the liquid by the agitators to produce very small bubbles, approximately 2 mm diameter average. The partial pressure of methanol in the nitrogen gas in the bottom section of the column is about 1 mm Hg. The pressure at the top of the column is approximately atmospheric, about 760 mm Hg, and the pressure at the bottom of the column is about 0.6 psig, i.e., about 790 mm Hg. This reaction yields a product in which the sucrose degree of conversion is approximately 94.4%.

EXAMPLE 2

This example uses the same reactor design and conditions as Example 1, with the exception of agitator speed. Agitator speed determines the degree of dispersion of the nitrogen in the liquid, and therefore how much liquid/vapor surface area is available for the mass transfer of methanol from the liquid to the stripping gas. Three separate reactions are performed using the same conditions for the agitator speed. Specifically, the agitator speed for the three reactions is 300 rpm, 500 rpm, and 600 rpm, respectively. The results of these three reactions are as follows:

| Agitator RPM | % Esterification | % Sucrose Octaester |
| --- | --- | --- |
| 300 | 95.6 | 65 |
| 500 | 96.3 | 70 |
| 600 | 97.8 | 82 |

This example shows that higher agitation speeds lead to improved conversion as a result of improved contact between the liquid and the gas.

EXAMPLE 3

This example uses a glass column reactor, 12-inches in diameter and 72-inches in length. The section plates are similar to the plates in Example 1, i.e., small holes in the plates allow upward travel of the gas, while liquid flow is directed through overflow weirs and downcomer tubes. There are six section plates in this column, and each section has a six-bladed turbine agitator having a diameter approximately one-half the diameter of the column. The molar ratio of total fatty acid methyl esters to sucrose in the column is 11:1. Two separate reactions are run in this column, one having a lower agitation rate, but higher gas/liquid ratio, the second having a higher agitation rate, but a lower gas/liquid ratio. The liquid residence time for each reaction is approximately 2 hours. The results of these two reactions are as follows:

| Agitator rpm | Gas/Liquid weight ratio | % Esterification | % Sucrose Octaester |
| --- | --- | --- | --- |
| 300 | 3:1 | 96.8 | 74 |
| 380 | 1.5:1 | 96.3 | 70 |

The conversions are very similar, even though the first reaction used twice the gas liquid ratio as the second reactor. This example shows that efficient dispersion of the gas in the reaction liquid can lead to reduced levels of inert gas required to drive the reaction to high conversion.

EXAMPLE 4

This example demonstrates running the transesterification reaction in a series of continuous stirred tank reactors (CSTR's), at atmospheric pressure with nitrogen sparging.

The reaction system comprises five 35 gallon reactors in series with associated pumps, agitators, heat exchangers and storage tanks. The reactors are supplied with nitrogen for sparging the continuous reaction at atmospheric pressure. Sucrose, fatty acid methyl esters, potassium carbonate, and potassium stearate are continuously fed into the first reactor. Additional fatty acid methyl esters and potassium carbonate are fed into the second and third reactors. Each reactor is recirculated with a recirculation pump, and product from each reactor is drawn off at approximately the same rate as material is fed in, so that the level in each reactor is maintained constant. The reactors are connected together in series, so that the product drawn off from the first reactor is fed into the second reactor, the product drawn off from the second reactor is fed into the third reactor, the product drawn off from the third reactor is fed into the fourth reactor, and the product drawn off from the fourth reactor is fed into the fifth reactor. The product from the fifth reactor is the final product, and is pumped into a product tank.

The molar ratio of potassium stearate soap-to-sucrose fed into the first reactor is about 0.05:1. The fatty acid methyl ester-to-sucrose molar ratio is about 5:1 in the first reactor, about 9:1 in the second reactor and about 11:1 in the third, fourth and fifth reactors, based on the sucrose employed in the first reactor. As noted above, additional fatty acid methyl esters are added to the second and third reactors to bring the total fatty acid methyl ester-to-sucrose ratios (based on number of moles of sucrose initially added to the first reactor) to these ratios. Additional potassium carbonate is added to the second and third reactors to bring the potassium carbonate-to-sucrose ratios therein to about 0.1:1 in the second reactor and about 0.2:1 in the third, fourth and fifth reactors. The temperature in each reactor is about 135° C., the agitator speed in each reactor is about 600 rpm, and the residence times are about 1.5 hours in the first reactor, and about 1 hour each in the remaining four reactors.

The nitrogen sparging gas was employed in increasing amounts from the first to fifth reactors, with the nitrogen gas:liquid weight ratio ranging from about 1:1 in the first reactor to about 2:1 in the fifth reactor. Additionally, the partial pressure of methanol in the nitrogen gas ranged from about 20 mm Hg in the first reactor to 0.8 mm Hg in the fifth reactor.

The product from the first reactor contains about 6 weight % sucrose, and each transesterified sucrose has, on average, about 3 fatty acid chains esterified thereto. The product from the second reactor contains less than about 1 weight % sucrose, and each transesterified sucrose has, on average, about 4 fatty acid chains esterified thereto. The product from the fifth (final) reactor has no detectable sucrose, and about 95 % of the original sucrose hydroxyl groups are esterified.

The specific and preferred embodiments provided herein are set forth to illustrate the invention and are not intended to limit the scope of the methods of the present invention. Additional embodiments and advantages within the scope of the claimed invention will be apparent to one of ordinary skill in the art.

What is claimed is:

1. A method for the solvent-less transesterification of sucrose, comprising reacting sucrose with fatty acid alkyl ester in the presence of a basic catalyst to produce sucrose fatty acid polyester product and lower alkyl alcohol by-product, wherein a majority of the sucrose is converted to octaester and the reaction is conducted in a reactor at a temperature in the range of from about 60° to about 180° C. and at atmospheric or superatmospheric pressure, and sparging an inert gas through the reactor with sufficient mass transfer surface area contact between the inert gas and a liquid mixture of reactant and product to transfer lower alkyl alcohol by-product from the liquid mixture to the inert gas and promote conversion of a majority of the sucrose to octaester without the use of vacuum pressure.

2. A method as defined by claim 1, wherein the reaction is conducted at an average reactor pressure of from about 760 mm Hg to about 2500 mm Hg.

3. A method as defined by claim 1, wherein the reaction is conducted at an average reactor pressure of from about 760 mm Hg to about 1500 mm Hg.

4. A method as defined by claim 1, wherein the transesterification reaction is conducted in a packed column reactor.

5. A method as defined by claim 1, wherein the transesterification reaction is conducted in a falling film reactor.

6. A method as defined by claim 1, wherein the transesterification reaction is conducted in at least one tank reactor provided with gas dispersers and agitators which disperse the inert gas into the liquid mixture.

7. A method as defined by claim 1, wherein the transesterification reaction is conducted in a multistage column reactor having counter current liquid and gas transfer means between stages.

8. A method as defined by claim 1, wherein inert gas containing the lower alkyl alcohol by-product is removed from the reactor, substantially all of the lower alkyl alcohol by-product is removed from the inert gas and at least a portion of the inert gas is recycled to the reactor.

9. A method as defined by claim 8, wherein the inert gas which is recycled has a lower alkyl alcohol partial pressure of less than about 10 mm Hg.

10. A method as defined by claim 1, wherein at least about 70 weight percent of the sucrose is converted to the octaester.

11. A method as defined by claim 1, wherein the degree of conversion of the sucrose hydroxyl groups to ester groups is at least 95 percent.

12. A method as defined by claim 1, wherein the fatty acid lower alkyl esters comprise fatty acid methyl esters and the alcohol by-product is methanol.

13. A method as defined by claim 1, wherein the transesterification is conducted in the presence of an emulsifier.

14. A method for the solvent-less transesterification of a polyol, comprising reacting polyol with fatty acid alkyl ester in the presence of a basic catalyst to produce polyol fatty acid polyester product and lower alkyl alcohol by-product, wherein a majority of the polyol is fully esterified and the reaction is conducted in a reactor at a temperature in the range of from about 60° to about 180° C. and at atmospheric or superatmospheric pressure, and sparging an inert gas through the reactor with sufficient mass transfer surface area contact between the inert gas and a liquid mixture of reactant and product to transfer the lower alkyl alcohol by-product from the liquid mixture to the inert gas and promote full esterification of a majority of the polyol without the use of vacuum.

15. A method as defined by claim 14, wherein the reaction is conducted at an average reactor pressure of from about 760 mm Hg to about 2500 mm Hg.

16. A method as defined by claim 14, wherein the reaction is conducted at an average reactor pressure of from about 760 mm Hg to about 1500 mm Hg.

17. A method as defined by claim 14, wherein the transesterification reaction is conducted in a packed column reactor.

18. A method as defined by claim 14, wherein the transesterification reaction is conducted in a falling film reactor.

19. A method as defined by claim 14, wherein the transesterification reaction is conducted in at least one tank reactor provided with gas dispersers and agitators.

20. A method as defined by claim 14, wherein the transesterification reaction is conducted in a multistage column reactor having counter current liquid and gas transfer means between stages.

21. A method as defined by claim 14, wherein inert gas containing the lower alkyl alcohol by-product is removed from the reactor, substantially all of the lower alkyl alcohol by-product is removed from the inert gas and at least a portion of the inert gas is recycled to the reactor.

22. A method as defined by claim 21, wherein the inert gas which is recycled has a lower alkyl alcohol partial pressure of less than about 10 mm Hg.

23. A method as defined by claim 14, wherein the polyol has at least three hydroxyl groups.

24. A method as defined by claim 14, wherein the polyol has at least four hydroxyl groups.

25. In a method for the transesterification of sucrose by solvent-less reaction of sucrose with fatty acid alkyl ester in the presence of a basic catalyst to produce sucrose fatty acid polyester product and lower alkyl alcohol by-product, wherein a majority of the sucrose is converted to octaester, the reaction being conducted in a reactor at a temperature in the range of from about 60° to about 180° C., the improvement comprising conducting the reaction at atmospheric or superatmospheric pressure and sparging an inert gas through the reactor with sufficient mass transfer surface area contact between the inert gas and a liquid mixture of reactant and product to transfer lower alkyl alcohol by-product from the liquid mixture to the inert gas and promote conversion of a majority of the sucrose to octaester without the use of vacuum pressure.

26. In a method for the transesterification of a polyol by solvent-less reaction of the polyol with fatty acid alkyl ester in the presence of a basic catalyst to produce polyol fatty acid polyester product and lower alkyl alcohol by-product, wherein a majority of the polyol is fully esterified, the reaction being conducted in a reactor at a temperature in the range of from about 60° to about 180° C., the improvement comprising conducting the reaction at atmospheric or superatmospheric pressure and sparging an inert gas through the reactor with sufficient mass transfer surface area contact between the inert gas and a liquid mixture of reactant and product to transfer the lower alkyl alcohol by-product from the liquid mixture to the inert gas and promote full esterification of a majority of the polyol without the use of vacuum pressure.

* * * * *